US007422747B2

(12) United States Patent
Langridge et al.

(10) Patent No.: US 7,422,747 B2
(45) Date of Patent: Sep. 9, 2008

(54) TRANSGENIC PLANT-BASED VACCINES

(75) Inventors: William H. R. Langridge, Loma Linda, CA (US); Jie Yu, Camarillo, CA (US); Takeshi Arakawa, Okinawa (JP)

(73) Assignee: Loma Linda University, Loma Linda, CA (US)

( * ) Notice: Subject to any disclaimer, the term of this patent is extended or adjusted under 35 U.S.C. 154(b) by 50 days.

(21) Appl. No.: 11/370,697

(22) Filed: Mar. 7, 2006

(65) Prior Publication Data

US 2006/0277635 A1 Dec. 7, 2006

Related U.S. Application Data

(60) Continuation-in-part of application No. 10/920,648, filed on Aug. 17, 2004, now abandoned, which is a continuation of application No. 09/296,981, filed on Apr. 22, 1999, now Pat. No. 6,777,546, and a continuation-in-part of application No. 09/167,493, filed on Oct. 7, 1998, now abandoned, and a continuation of application No. 11/001,153, filed on Nov. 30, 2004, now abandoned, which is a continuation of application No. 10/245,749, filed on Sep. 16, 2002, now abandoned, which is a division of application No. 09/771,536, filed on Jan. 29, 2001, now abandoned.

(60) Provisional application No. 60/178,403, filed on Jan. 27, 2000, provisional application No. 60/082,688, filed on Apr. 22, 1998, provisional application No. 60/061,265, filed on Oct. 7, 1997.

(51) Int. Cl.
*A61K 39/00* (2006.01)

(52) U.S. Cl. .................................................. 424/184.1

(58) Field of Classification Search ............... 424/184.1
See application file for complete search history.

(56) References Cited

U.S. PATENT DOCUMENTS

| | | | | |
|---|---|---|---|---|
| 4,879,113 | A | 11/1989 | Smith | 424/88 |
| 4,956,282 | A | 9/1990 | Goodman et al. | 435/69.51 |
| 5,079,165 | A | 1/1992 | Clements et al. | 435/252.8 |
| 5,098,998 | A | 3/1992 | Mekalanos et al. | 530/350 |
| 5,268,276 | A | 12/1993 | Holmgren et al. | 435/69.1 |
| 5,308,835 | A | 5/1994 | Clements | 514/12 |
| 5,484,719 | A | 1/1996 | Lam et al. | 435/172.3 |
| 5,589,384 | A | 12/1996 | Lipscombe et al. | 435/252.33 |
| 5,612,487 | A | 3/1997 | Lam et al. | 800/205 |
| 5,628,994 | A | 5/1997 | Kaper et al. | 424/93.2 |
| 5,654,184 | A | 8/1997 | Curtiss, III et al. | 435/172.3 |
| 5,679,880 | A | 10/1997 | Curtiss, III et al. | 800/205 |
| 5,681,571 | A | 10/1997 | Holmgren et al. | 424/236.1 |
| 5,686,079 | A | 11/1997 | Curtiss, III et al. | 424/234 |
| 5,698,416 | A | 12/1997 | Wolf et al. | 435/69.1 |
| 5,789,245 | A | 8/1998 | Dubensky, Jr. et al. | 435/320.1 |
| 5,869,057 | A | 2/1999 | Rock | 424/192.1 |
| 5,891,432 | A | 4/1999 | Hoo | 424/93.21 |
| 5,917,026 | A | 6/1999 | Löwenadler et al. | 536/23.4 |
| 6,015,694 | A | 1/2000 | Dubensky, Jr. et al. | 435/69.3 |
| 6,030,624 | A | 2/2000 | Russell et al. | 424/200.1 |
| 6,036,953 | A | 3/2000 | Ryan et al. | 424/93.2 |
| 6,110,724 | A | 8/2000 | Nakagomi et al. | 435/235.1 |
| 6,194,560 | B1 | 2/2001 | Arntzen et al. | 536/23.7 |
| 6,395,964 | B1 | 5/2002 | Arntzen et al. | 800/288 |
| 6,589,529 | B1 * | 7/2003 | Choi et al. | 424/186.1 |

FOREIGN PATENT DOCUMENTS

| | | |
|---|---|---|
| EP | 0437320 A1 | 7/1991 |
| WO | WO9200099 | 1/1992 |
| WO | WO9310246 | 5/1993 |
| WO | WO9508347 | 3/1995 |
| WO | WO9508633 | 3/1995 |
| WO | WO9611708 | 4/1996 |
| WO | WO 96/12801 | 5/1996 |
| WO | WO9626218 | 8/1996 |
| WO | WO9823763 | 6/1998 |
| WO | WO09954452 | 10/1999 |

OTHER PUBLICATIONS

Gonzalez et al, Immunological characterization of a rotavirus-neutralizing epitope fused to the cholera toxin B subunit. Gene. Nov. 15, 1993;133(2):227-32.*

Shi et al, Gene fusion of cholera toxin B subunit and HBV PreS2 epitope and the antigenicity of fusion protein. Vaccine. Jul. 1995;13(10):933-7.*

Plotkin et al (Vaccines WB Saunders Company 1988, p. 571).*

Arakawa, T. et al., "A plant-based cholera toxin B subunit-insulin fusion protein protects against the development of autoimmune diabetes," *Nature Biotechnology*, 16:934-938, Oct. 1998.

Arakawa, T., "Suppression of Autoimmune Diabetes by a Plant-Delivered Cholera Toxin B Subunit-Human Glutamate Decarboxylase Fusion Protein," *Transgenics*, 3:51-60 (1999).

Arakawa, T. et al., "Expression of cholera toxin B-subunit oligomers in transgenic potato plants," *Transgenic Research*, 6:403-413, 1997.

Bergerot,. et al., "A cholera toxoid-insulin conjugate as an oral vaccine against spontaneous autoimmune diabetes," *Proc. Nat'l. Acad. Sci. USA*, 94:4610-4614 (Apr. 1997).

De Neve, M. et al., Gene silencing results in instability of antibody production in transgenic plants, *Mol. Gen. Genet*, 260:582-592 (1999).

Dertzbaugh, M. et al., "Comparative Effectiveness of the Cholera Toxin B Subunit and Alkaline Phosphatase as Carriers for Oral Vaccines," *Infection and Immunity*, 61(1):48-55 (Jan. 1993).

Doherty, P.C. et al., "CD8+ T-cell memory to viruses," *Current Opinion in Immunology*, 6:545-552 (1994).

Fromm et al., "Inheritance and Expression of Chimeric Genes in the Progeny of Transgenic Maize Plants," *Biotechnology*, vol. 8, 1990, pages.

(Continued)

*Primary Examiner*—Mark Navarro
(74) *Attorney, Agent, or Firm*—David A. Farah; Sheldon Mak Rose & Anderson PC

(57) ABSTRACT

A method of inducing partial or complete immunity to an infectious disease in a mammal comprising providing to the mammal for oral consumption an effective amount of a protein complex comprising five monomeric fusion proteins.

3 Claims, 2 Drawing Sheets

OTHER PUBLICATIONS

Gilbert, S.C. et al., "A protein particle vaccine containing multiple malaria epitopes," *Nature Biotechnology*, 15:1280-1284 (Nov. 1997).

Hajishengallis G. et al., "Muscosal Immunication With a Bacterial Protein Antigen Genetically Coupled to Cholera Toxin A2/B Subunits," Journal of Immunology, The Williams and Wilkins Co., Baltimore, MD, vol. 154, No. 9, 1995, pp. 4322-4332.

Hao, T. et al., "Oral Immunization with a Recombinant Bacterial Antigen Produced in Transgenic Plants," *Science*, 268:714-716 (May 1995).

Hardy,S.J.S. et al., "Coordinated assembly of multisubunit proteins: Oligomerization of bacterial enterotoxins in vivo and in vitro," *Proc. Natl. Acad. Sci. USA*, 85:7109-7113 (Oct. 1988).

Hein, M.B. et al., "Expression of Cholera Toxin Subunits in Plants," *Annuals of New York Academy of Sciences*, 792:50-56 (May 1996).

Holgren, J. et al., "Strategies for the Induction of Immune Responses at Mucosal Surfaces Making Use of Cholera Toxin B Subunit as Immunogen, Carrier, and Adjuvant," *Am. J. Prop. Med. Hyg.*, 42-54 (1994).

Jackson, Raymond J., "Optimizing Oral Vaccines: Induction of Systemic and Mucosal B-Cell and Antibody Responses to Tetanus Toxoid by use of Cholera Toxin as an Adjuvant," *Infection and Immunity*, 61(10):4272-4279 (Oct. 1993).

Jefferson, Richard et al., "GUS fusions: β-glucuronidse as a sensitive and versatile gene fusion marker in higher plants," *EMBO Journal*, 6(13):3901-3907 (Dec. 1987).

Liljeqvist S. et al., "Production of Recombinant Subunit Vaccines: Protein Immunogens, Live Delivery Systems and Nucleic Acid Vaccines," Journal of Biotechnology, Elsevier Science Publishers, Amsterdam, NL, vol. 73, No. 1, 1999, pp. 1-33.

Lowe, Keith et al., "Germline Transformation of Maize Following Manipulation of Chimeric Shoot Meristems," *Biotechnology*, 13:677-682 (Jul. 1995).

Ma, S.W., "Transgenic plants expressing autoantigens fed to mice to induce oral immune tolerance," *Nature Medicine*, 3(7):793-796 (Jul. 1997).

Mason, H.S., "Transgenic plants as vaccine production systems," *Tibtech*, 13:388-392 (Sep. 1995).

McInerney, T.L. et al., "Analysis of the ability of five adjuvants to enhance immune responses to a chimeric plant virus displaying an HIV-1 peptide," *Vaccine*, 17:1359-1368 (1999).

Modelska, Anna et al., "Immunization against rabies with plant-derived antigen", *Proc. Natl. Acad. Sci. USA*, 95:2481-2485 (Mar. 1998).

Mowat, A.M., "Oral tolerance therapy fundamental and practical aspects," *Chemistry & Industry*, pp. 10-9 (Nov. 1996).

Nashar,T.O. et al., "Current progress in the development of the B subunits of cholera toxin and *Escherichia coli* heat-labile enterotoxin as carriers for the oral delivery of heterologous antigens and epitopes," *Vaccine*, 11(2):235-240 (1993).

Schon, A. et al., "Thermodynamics of Intersubunit Interactions in Cholera Toxin upon Binding to the Oligosaccharide Portion of Its Cell Surface Receptor, Ganglioside $G_{M1}$" *Biochemistry*, 28:5019-5024 (1989).

Sedlik, C. et al., "Recombinant parvovirus-like particles as an antigen carrier: A novel nonreplicative exogenous antigen to elicit protective antiviral cytotoxic T cells," *Proc. Natl. Acad. Sci. USA*, 94:7503-7508 (Jul. 1997).

Simone, E.A. et al., "Immunologic 'Vaccination' for the Prevention of Autoimmune Diabetes (Type 1A)," *Diabetes Care*, 22(2):B7-B15 (Mar. 1999).

Spangler, B.D., "Structure and Function of Cholera Toxin and the Related *Escherichia coli* Heat-Labile Enterotoxin," *Microbiological Reviews*, 56:(4)622-647 (Dec. 1992).

Sun, J., et al., "Cholera toxin B subunit: An efficient transmucosal carrier-delivery system for induction of peripheral immunological tolerance," *Proc. Natl. Acad. Sci. USA*, 91:10795-10799 (Nov. 1994).

Williams, Neil A. et al., "Immune modulation by the cholera-like enterotoxins: from adjuvant to therapeutic," *Immunology Today*,(Feb. 1999).

* cited by examiner

TRANSGENIC PLANT-BASED VACCINES

CROSS-REFERENCE TO RELATED APPLICATION

The present application is a continuation-in-part of U.S. patent application Ser. No. 10/920,648, titled "Methods and Substances for Preventing and Treating Autoimmune Disease," filed Aug. 17, 2004, now abandoned, which is a continuation of U.S. patent application Ser. No. 09/296,981, titled "Methods and Substances for Preventing and Treating Autoimmune Disease," filed Apr. 22, 1999, now U.S. Pat. No. 6,777,546, issued on Aug. 17, 2004, which: 1) claims the benefit of U.S. Patent Application No. 60/082,688, titled "Plant Vaccines Against Autoimmune Disease," filed Apr. 22, 1998 and 2) is a continuation-in-part of U.S. patent application Ser. No. 09/167,493, titled "Expression of Cholera Toxin B Subunit in Transgenic Plants and Efficacy Thereof in Oral Vaccines," filed Oct. 7, 1998, now abandoned, which claims the benefit of U.S. Patent Application No. 60/061,265, titled "Cholera Toxin in Food Plants," filed Oct. 7, 1997; and the present application is a continuation of U.S. patent application Ser. No. 11/001,153, titled "Transgenic Plant-based Vaccines," filed Nov. 30, 2004, now abandoned, which is a continuation of U.S. patent application Ser. No. 10/245,749, titled "Transgenic Plant-based Vaccines," filed Sep. 16, 2002, now abandoned , which is a divisional of U.S. patent application Ser. No. 09/771,536, filed Jan. 29, 2001 now abandoned, which claims the benefit of U.S. Patent Application 60/178,403, titled "Production of a Cholera Toxin B Subunit-rotavirus NSP4 Enterotoxin Fusion Protein in Potato," filed Jan. 27, 2000; the contents of which are incorporated by reference herein in their entirety.

STATEMENT REGARDING FEDERALLY SPONSORED RESEARCH OR DEVELOPMENT

This invention was made with United States Government support under subcontract number 010-FY97-LLU-LANGRIDGE with the National Medical Test Bed, United States Department of the Army. The United States Government has certain rights in this invention.

BACKGROUND

Acute infectious enteric diseases, such as acute gastroenteritis, are second only to acute respiratory diseases as a cause of human death worldwide. Cholera, rotavirus and enterotoxigenic *E. coli* are the three major causative agents of acute gastroenteritis. Human rotavirus, for example, is the most important cause of infantile gastroenteritis worldwide. This virus has a tremendous public health impact worldwide, infecting nearly every child in the first few years of life. Rotavirus infection is responsible for approximately 1 million deaths each year and an estimated 18 million hospitalizations. 20% to 40% of the hospitalizations are for childhood diarrhea, which makes the rotavirus the most important single cause of diarrheal mortality among children.

Treatment for acute gastroenteritis includes antibiotics and metabolic support. However, adequate treatment is often not available, particularly in lesser developed areas where the incidence of acute gastroenteritis is highest. Prevention of acute gastroenteritis would be preferable to treatment. However, preventative measures, such as the provision of safe drinking water, are often inadequate or unavailable.

Therefore, it would be useful to have a new method for the prevention of acute gastroenteritis. Further, it would be particularly useful to have a method for the prevention of acute gastroenteritis which would prevent multiple types of acute gastroenteritis simultaneously.

SUMMARY

According to one embodiment of the present invention, there is provided a DNA construct that encodes, upon expression in a plant cell, a fusion protein comprising a multimeric cholera toxin B subunit and a first immunogenic antigen from a causal factor of a first mammalian disease. The first immunogenic antigen can be a rotavirus antigen. The first immunogenic antigen can also be an enterotoxigenic *E. coli* antigen.

The fusion protein encoded by the DNA construct can further comprise a second cholera toxin subunit. The second cholera toxin subunit can be cholera toxin A2 subunit.

The fusion protein encoded by the DNA construct can further comprise a second immunogenic antigen from a causal factor of a second mammalian disease. The second immunogenic antigen can be a rotavirus antigen. The second immunogenic antigen can also be an enterotoxigenic *E. coli* antigen. Either the first mammalian disease or the second mammalian disease or both can be an infectious enteric disease.

According to another embodiment of the present invention, there is provided a DNA construct that encodes, upon expression in a plant cell, a fusion protein comprising a cholera toxin A2 subunit, a multimeric cholera toxin B subunit, a first immunogenic antigen from a causal factor of a first mammalian disease, and a second immunogenic antigen from a causal factor of a second mammalian disease. The first immunogenic antigen can be a rotavirus antigen. The second immunogenic antigen can be an enterotoxigenic *E. coli* antigen. Either the first mammalian disease or the second mammalian disease or both can be an infectious enteric disease.

According to another embodiment of the present invention, there is provided an expression vector comprising a DNA construct of the present invention, a transgenic plant cell transformed with a DNA construct of the present invention, a transgenic plant seed transformed with the DNA construct of the present invention, and a transgenic plant transformed with the DNA construct of the present invention.

According to yet another embodiment of the present invention, there is provided a method of producing an immunogen in a plant comprising cultivating a transgenic plant of the present invention under conditions effective to express the fusion protein.

According to another embodiment of the present invention, there is provided a method of inducing partial or complete immunity to an infectious disease in a mammal comprising providing to the mammal for oral consumption an effective amount of a plant of the present invention.

The present invention also includes means for producing, in a plant cell, a fusion protein comprising a multimeric cholera toxin B subunit and a first immunogenic antigen from a causal factor of a first mammalian disease. The means can comprise a DNA construct that encodes, upon expression in the plant cell, a multimeric cholera toxin B subunit and a first immunogenic antigen from a causal factor of a first mammalian disease. The first immunogenic antigen can be a rotavirus antigen. The first immunogenic antigen can also be an enterotoxigenic *E. coli* antigen. The fusion protein can further comprise a second cholera toxin subunit, such as cholera toxin A2 subunit. The fusion protein can further comprise a second immuhogenic antigen from a causal factor of a second mammalian disease. The second immunogenic antigen can be a rotavirus antigen. The second immunogenic antigen can also be an enterotoxigenic *E. coli* antigen.

The present invention also includes means for producing, in a plant cell, a fusion protein comprising a cholera toxin A2 subunit, a multimeric cholera toxin B subunit, a first immunogenic antigen from a causal factor of a first mammalian disease, and a second immunogenic antigen from a causal factor of a second mammalian disease. The first immunogenic antigen can be a rotavirus antigen. The second immunogenic antigen can be an enterotoxigenic *E. coli* antigen.

According to another embodiment of the present invention, there is provided an expression vector comprising the means of the present invention, a transgenic plant cell transformed with means of the present invention, a transgenic plant seed transformed with the means of the present invention, and a transgenic plant transformed with the means of the present invention.

The present invention also includes a method of producing an immunogen in a plant comprising cultivating the transgenic plant of the present invention under conditions effective to express the fusion protein. The present invention further includes a method of inducing partial or complete immunity to an infectious disease in a mammal comprising providing to the mammal for oral consumption an effective amount of a plant of the present invention.

According to another embodiment of the present invention, there is provided a fusion protein comprising a multimeric cholera toxin B subunit and a first immunogenic antigen from a causal factor of a mammalian disease. The first immunogenic antigen can be a rotavirus antigen. The first immunogenic antigen can also be an enterotoxigenic *E. coli* antigen. The fusion protein can further comprise a second cholera toxin subunit. The second cholera toxin subunit can be cholera toxin A2 subunit. The fusion protein can further comprise a second immunogenic antigen from a causal factor of a second mammalian disease. The second immunogenic antigen can be a rotavirus antigen. The second immunogenic antigen can also be an enterotoxigenic *E. coli* antigen. Either the first mammalian disease or the second mammalian disease or both can be an infectious enteric disease.

In one embodiment, the fusion protein comprises a cholera toxin A2 subunit, a multimeric cholera toxin B subunit, a first immunogenic antigen from a causal factor of a mammalian disease, and a second immunogenic antigen from a causal factor of a second mammalian disease.

According to another embodiment of the present invention, there is provided a fusion protein encoded by the DNA construct of the present invention.

According to another embodiment of the present invention, there is provided a method of inducing partial or complete immunity to an infectious disease in a mammal comprising providing to the mammal for oral consumption an effective amount of the fusion protein of the present invention.

FIGURES

The features, aspects and advantages of the present invention will become better understood with regard to the following description, appended claims and accompanying figures where:

DESCRIPTION

According to one embodiment of the present invention, there is provided a method of inducing partial or complete immunity to an infectious disease, such as gastroenteritis, in a mammal by administering to the mammal a portion of a transgenic plant comprising a fusion protein, where the fusion protein comprises at least one cholera toxin subunit and an immunogenic antigen from a causal factor of the disease. In a preferred embodiment, the fusion protein comprises at least two cholera toxin subunits, at least one of which functions as an antigen, in addition to functioning as an adjuvant for the immunogenic antigen. In another preferred embodiment, the fusion protein comprises at least two immunogenic antigens, each fused to a cholera toxin subunit. By fusing the immunogenic antigen to the cholera toxin subunit, the fusion protein more specifically targets the appropriate immune system tissue upon administration. This increased specificity compensates for the low level of production of the protein in the transgenic plant and increases the response of the mammal's immune system.

In one embodiment, the fusion protein comprises the twenty-two amino acid immunodominant epitope of the murine rotavirus enterotoxin NSP4 fused to the cholera toxin B subunit (CTB). In another embodiment, the fusion protein comprises the enterotoxigenic *E. coli* (ETEC) fimbrial colonization factor CFA/I fused to the cholera toxin A2 subunit (CTA2). In yet another embodiment, the fusion protein comprises both the twenty-two amino acid immunodominant epitope of the murine rotavirus enterotoxin NSP4 fused to the cholera toxin B subunit, and the fusion protein comprises the enterotoxigenic *E. coli* fimbrial colonization factor CFA/I fused to the cholera toxin A2 subunit.

Though the method is described in the context of preventing gastroenteritis by way of example, it will be understood by those with skill in the art with reference to this disclosure, that the present method can be used to prevent other enteric infectious diseases and other non-enteric infectious diseases such as respiratory diseases. The method will now be described in more detail.

1) Construction of a Transgenic Plant Producing a Fusion Protein Comprising the Immunodominant Epitope of the Murine Rotavirus Enterotoxin NSP4 Fused to the Cholera Toxin B Subunit and Confirmation of Transformation.

According to one embodiment of the present invention, there is provided a transgenic plant producing a fusion protein comprising the twenty-two amino acid immunodominant epitope of the murine rotavirus enterotoxin NSP4 fused to the cholera toxin B subunit. The transgenic plant can be administered to a mammal to immunize the mammal against cholera and rotavirus infection simultaneously.

Figure 1:
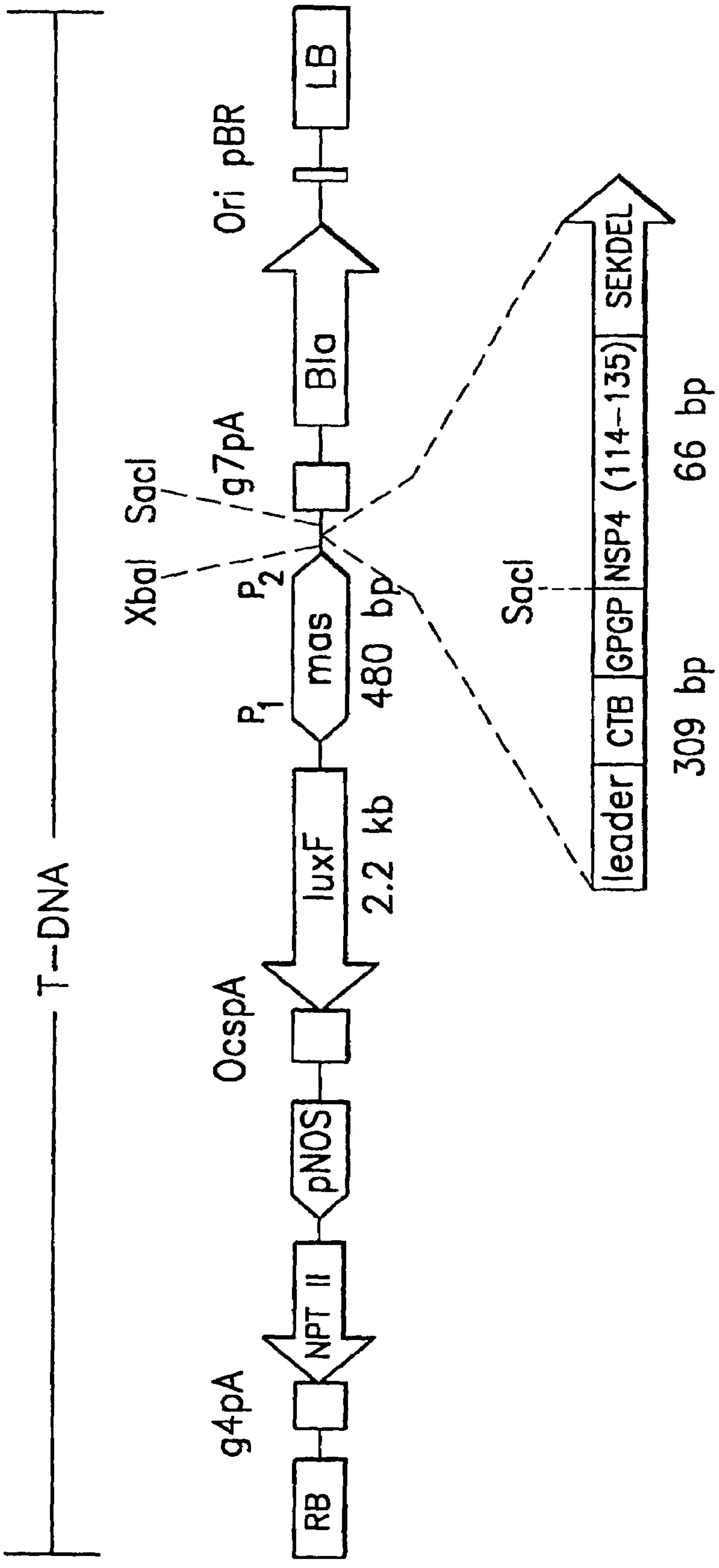
FIG. 1 is a diagram of the vector pPCV701FM4-CTB: NSP4.

Referring now to FIG. 1, there is shown a diagram of the vector used to prepare the transgenic plant. As can be seen, the vector contained four genes located within the transferred DNA (T-DNA) sequence flanked by the right and left border (RB and LB), and 25 bp direct repeats of the borders required for integration of the transferred DNA into plant genomic DNA. The four genes were the CTBH:NSP4(114-135): SEKDEL coding sequence under control of the mas P2 promoter; the bacterial luciferase AB fusion gene (luxF) under control of the mas P1 promoter used as a detectable marker; an NPT II expression cassette used for resistance to kanamycin in plants; and a β-lactamase cassette for resistance to ampicillin in *E. coli* and carbenicillin in *A. tumefaciens*. The g7pA polyadenylation signal was from the *A. tumefaciens* $T_L$-DNA gene 7. The OcspA polyadenylation signal is from the octopine synthase gene. Pnos was the promoter of the nopaline synthase gene g4pA was the polyadenylation signal from $T_L$-DNA gene 4. OriT was the origin of transfer derived from pRK2. OriV was the wide host range origin of replication for multiplication of the plasmid in *A. tumefaciens* derived from pRK2. Ori pBR322 was the replication origin of pBR322 for maintenance of the plasmid in *E. coli*.

The vector pPCV701FM4-CTB:NSP4 was constructed as follows. The plant expression vector pPCV701FM4, a derivative of plasmid pPCV701, was digested with XbaI and SacI restriction endonucleases within the multiple cloning site to insert a gene encoding the cholera toxin B subunit and its leader sequence, SEQ ID NO:1, from plasmid pRT42 containing the ctxAB operon. The oligonucleotide 5' primer (5'-gctctagagccaccatgattaaattaaaatttggtg-3'), SEQ ID NO:2, and the 3' primer (5'-ctggagctcgggccccggcccatttgccatactaattgcgg-3'), SEQ ID NO:3, were synthesized with XbaI and SacI restriction endonuclease recognition sites (bold) for amplification and cloning of the CTB-hinge coding sequence, SEQ ID NO:4, in a model 394 DNA/RNA Synthesizer (Applied Biosystems, Inc. Foster City, Calif. US)

The oligonucleotide sequence surrounding the translation initiation codon of the CTB gene, SEQ ID NO:1, was altered to a preferred nucleotide context for translation in eukaryotic cells, (5'-gccacc-3') and a putative Shine-Dalgarno sequence (AGGA) present in the ctxAB operon in plasmid pPT42 was removed. The DNA sequence, SEQ ID NO:5, encoding the 21 amino acid leader peptide of the CTB was retained to direct the nascent CTB fusion peptide into the lumen of the ER.

The 3' primer, SEQ ID NO:3, was designed to contain a nucleotide sequence encoding a Gly-Pro box (Gly-Pro-Gly-Pro) with relatively less frequently used codons in plants to allow the ribosomes to halt for proper folding of CTB moiety before translation of the downstream message sequence. An additional function of the Gly-Pro box was to act as a flexible hinge between CTB and the conjugated peptide.

The methods for cloning the CTBH fusion gene, SEQ ID NO:4, into the multiple cloning site immediately downstream of the mas $P_2$ promoter and the DNA sequence confirmation were as follows. PCR amplification was performed using a Gene Amp PCR System 9600, (The Perkin Elmer Corporation, Norwalk, Conn. US) according to the following reaction parameters; 94° C., 45 sec.: 55° C. for 60 sec.: 72° C. for 45 sec., 30 cycles total. The ligated vector and PCRed fragment (T4 ligase at 16° C. for 20 hrs.) were electroporated into *Escherichia coli* strain HB101 (250 μFD, 200Ω, and 2,500 volts; BioRad® Gene Pulser II unit (Bio Rad Laboratories, Inc., Hercules, Calif. US) and ampicillin resistant colonies were isolated after overnight growth at 37° C.

To confirm the presence of the correct CTBH fusion gene sequence, SEQ ID NO:4, in transformed *E. coli* cells, the plasmid was isolated from individual colonies of transformants and subjected to DNA sequence analysis with the forward primer (5'- accaatacattacactagcatctg-3'), SEQ ID NO:6, specific for the mas $P_2$ promoter and the reverse primer (5'-gactgagtgcgatattatgtgtaatac-3'), SEQ ID NO:7, specific for the gene 7 poly(A) signal (model 373A DNA Sequencer, Applied Biosystems, Inc.). This plant transformation vector was designated as pPCV701FM4-CTBH.

To insert the rotavirus enterotoxin NSP4(114-135) epitope gene, SEQ ID NO:8, two overlapping primer sequences were synthesized and equimolar amounts of both single-stranded deoxyribonucleotide fragments were subjected to PCR amplification (94° C. 45 sec.: 55° C. for 60 sec.: 72° C. for 60 sec.: 30 cycles total) to create double stranded 103 bp length synthetic gene. The 5' oligonucleotide, SEQ ID NO:9,5'-gccgagctcgataagttgactactagggagattgagcaagttgagttgttgaagaggatt-3' and the 3' oligonucleotide, SEQ ID NO:10, 5'-gccgagctcacaactcatccttctcagaagtcaacttatcgtaaatcctcttcaacaact-3' were designed to contain 17 bp complementary sequence for the thermostable Vent DNA polymerase (New England Biolabs, Beverly, Mass. US) attachment site for the initial cycle of the PCR reaction. The 3' oligonucletide, SEQ ID NO:10, contained the DNA sequence encoding endoplasmic reticulum retention signal (SEKDEL) with codons most frequently found in potato plants. Both oligonucleotides contains SacI recognition sites (bold) to clone the synthetic gene fragment into SacI site immediately downstream of the hinge sequence of the vector to create vector pPCV701FM4-CTBH:NSP4.

Following confirmation of the correct fusion gene sequence, CTBH:NSP4(114-135):SEKDEL, SEQ ID NO:11, the shuttle vector was transferred into *A. tumefaciens* recipient strain GV3101 pMP90RK by the same electroporation conditions used for *E. coli* transformation. *A. tumefaciens* transformants were grown at 29° C. on YEB solid medium containing the antibiotics carbenicillin (100 μg/ml), rifampicin (100 μg/ml), kanamycin (25 μg/ml), and gentamycin (25 μg/ml) for selection of transformants.

The plasmid was isolated from an *A. tumefaciens* transformant and transferred back into *E. coli* HB101 by electroporation, and restriction endonuclease analysis was used to confirm that no significant deletion had occurred in the vector. Structural confirmation of the plasmid was required because recombination events within the $rec^+$ *A. tumefaciens* strain could alter the T-DNA sequence. Transfer of the plasmid from *A. tumefaciens* back to the *E. coli* host was necessary because significant amounts of plasmid are difficult to isolate directly from *A. tumefaciens*. Agrobacteria carrying the plant expression vector were grown on YEB solid medium containing all four antibiotics for 48 hours at 29° C. and directly used for transformation of sterile potato leaf explants.

Sterile potato plants *S. tuberosum* cv. Bintje were grown in Magenta boxes (Sigma Chemical Co., St. Louis, Mo. US) on solid Murashige and Skoog (MS) complete organic medium (JRH Biosciences, Lenexa, Kans. US) containing 3.0% sucrose and 0.2% gelrite. Leaf explants excised from the young plants were laterally bisected in a 9 cm diameter culture dish containing an overnight culture of *A. tumefaciens* suspension ($1\times10^{10}$ cell/ml) harboring pPCV701FM4-CTBH:NSP4. The bacterial suspension was supplemented with acetosyringone (370 μM) to increase transformation efficiency. The explants were incubated in the bacterial suspension for 5 minutes, blotted on sterile filter paper, and transferred to MS solid medium, pH 5.7, containing 0.1 μg/ml naphthalene acetic acid (NAA) and 1.0 μg/ml trans-zeatin. The leaf explants were then incubated for 48 hours at room temperature on MS solid medium to permit T-DNA transfer into the plant genome. For selection of transformed plant cells and for counter selection against continued *Agrobacterium* growth, the leaf explants were transferred to MS solid medium containing the antibiotics kanamycin (100 μg/ml) and claforan (300 μg/ml).

Transformed plant cells formed calli on the selective medium after continuous incubation for 2 to 3 weeks at room temperature in a light room under cool white fluorescent tubes on a 12 hour photoperiod regime. When transformed calli grew to between 5 mm and 10 mm in diameter, the leaf tissue was transferred to MS medium containing 1.0 μg/ml trans-zeatin, 50 μg/ml kanamycin and 400 μg/ml claforan for shoot induction. Regenerated shoots were excised and transferred to MS solid medium without plant hormones or antibiotics to stimulate root formation. Plantlets were allowed to grow and form microtubers under sterile conditions to characterization.

Luciferase activity was detected in transformed *A. tumefaciens* and transgenic plants as follows. The presence of the plant expression plasmid in agrobacteria, luxF gene expression under control of the mas P1 promoter was monitored by low-light image analysis. To perform the bioluminescent assay, bacterial culture grown for 24 hours on YEB solid culture medium was covered with a glass culture plate lid swabbed with substrate n-decyl aldehyde and analyzed by the Argus-100 intensified camera system (Hamamatsu Photonics UK Ltd., Bridgewater, N.J. US).

Expression of luxF gene was also monitored to confirm the presence of the CTBH:NSP4(114-135):SEKDEL, SEQ ID NO:11, in the plant genome and to estimate the level of CTB fusion gene expression by mas P2 promoter. Leaves excised from putative transformants were wounded by scalpel blade followed by incubation on MS solid medium containing naphthalene acetic acid (5 μg/ml) and 2,4-dichlorophenoxy acetic acid (6 μg/ml) for 48 hours. Light emission from the wounded leaf tissues was detected as described for agrobacteria.

More than forty independent kanamycin-resistant plants were regenerated from *Agrobacterium* mediated transformation of potato leaf explants with the plant expression vector pPCV701FM4-CTBH:NSP4. Three of the forty plants were found to express luciferase activities above background levels from untransformed plants. No luciferase activity was detected in leaves of untransformed potato plants.

The three transformed potato plants showing luciferase activities were analyzed for the presence of the fusion gene in plant genomic DNA isolated from young leaf tissues as follows. Genomic DNA was isolated from the transformed potato leaf tissues. Presence of the CTB fusion gene was determined by PCR analysis using the oligonucleotide primers specific for the T-DNA sequence. Transformed plant genomic DNA (500 ng) was used as a template to detect the CTB gene by PCR amplification (94° C. for 45 sec.: 55° C. for 60 sec.: 62° C. for 60 sec. for a total of 30 cycles). A 650 bp DNA fragment including both 5' and 3' flanking sequences of the fusion gene, was amplified. The PCR amplification was very specific probably due to high specificity of the primers used for the PCR reaction.

The DNA fragments amplified from plasmid vector pPCV701FM4-CTBH:NSP4 and from transgenic plant genomic DNA were identical in molecular weight. Although, identical amounts of template genomic DNA (500 ng) was used for the PCR reaction, the plant exhibiting the highest luciferase activity also demonstrated the highest level of PCR amplification.

The presence of the CTB fusion protein was detected in transformed potato tissues as follows. Transgenic potato leaf and microtuber tissues were analyzed for the CTB fusion gene expression by immunoblot analysis. Callus tissues were derived from leaf or tuber tissues incubated for 4 weeks on MS solid medium containing 5.0 mg/l NAA and 6.0 mg/l 2,4-D. Tissues were homogenized by grinding by a mortar and pestle at 4° C. in extraction buffer (1:1 w/v) (200 mM Tris-Cl, pH 8.0, 100 mM NaCl, 400 mM sucrose, 10 mM EDTA, 14 mM 2-mercaptoethanol, 1 mM phenylmethylsulfonyl fluoride, 0.05% Tween-20). The tissue homogenate was centrifuged at 17,000×g in a Beckman GS-15R centrifuge for 15 minutes at 4° C. to remove insoluble cell debris. An aliquot of supernatant containing 100 μg of total soluble protein, as determined by Bradford protein assay (Bio Rad Laboratories, Inc.), was separated by 15% sodium dodecylsulfate polyacrylamide gel electrophoresis (SDS-PAGE) at 125 volts for 30 to 45 minutes in Tris-glycine buffer (25 mM Tris, 250 mM glycine, pH 8.3, 0.1% SDS). Samples were either loaded directly on the gel or boiled for 5 minutes prior to electrophoresis.

The separated protein bands were transferred from the gel to approximately 80 $cm^2$ Immun-Lite membranes (Bio Rad Laboratories, Inc.) by electroblotting on a semi-dry blotter (Labconco, Kansas City, Mo. US) for 60 minutes at 15 V and 100 mA. Nonspecific antibody reactions were blocked by incubation of the membrane in 25 ml of 5% non-fat dry milk in TBS buffer (20 mM Tris pH 7.5 and 500 mM NaCl) for 1 hour with gentle agitation on a rotary shaker (40 rpm), followed by washing in TBS buffer for 5 minutes. The membrane was incubated overnight at room temperature with gentle agitation in a 1:5,000 dilution of rabbit anti-cholera antiserum (Sigma C-3062) in TTBS antibody dilution buffer (TBS with 0.05% Tween-20 and 1% non-fat dry milk) followed by washing three times in TBST washing buffer (TBS with 0.05% Tween-20). The membrane was incubated for 1 hour at room temperature with gentle agitation in a 1:10,000 dilution of mouse anti-rabbit IgG conjugated with alkaline phosphatase (Sigma A-2556) in antibody dilution buffer. The membrane was washed three times in TTBS buffer as before and once with TBS buffer, followed by incubation in 1× chemiluminescent substrate CSPD™ (Bio Rad Laboratories, Inc.) for 5 minutes at room temperature with gentle agitation. The membrane was then wrapped with transparent plastic membrane and placed in a photocassette on Kodak X-OMAT film (cat# 1651454). (The membrane was also used to image chemiluminescent light intensity in both the numerical and graphic form by the Argus-100 video image analysis.) The film was subjected to 1-10 minutes exposure and developed in a Kodak M35A X-OMAT Processor.

Using this method, transgenic potato tuber tissues from the three transformed plants were shown to contain CTB fusion protein (~60 kDa) that strongly reacted with anti-cholera toxin antibody which predominantly recognized pentameric form of cholera toxin or its B subunit. Potato plants transformed with the plant expression vector only, which did not contain the CTBH:NSP4(114-135):SEKDEL sequence, SEQ ID NO:11, did not show this protein band. One plant, designated Plant #1, showed approximately 3 to 5 fold higher chimeric protein level than the other two plants, Plant #2 and Plant #3. Potato-synthesized CTB-NSP4 fusion peptide exhibited higher molecular weight than both pentameric bacterial CTB subunit (45 kDa) and potato-synthesized pentameric CTB subunit with ER retention signal (50 kDa).

The level of CTB fusion protein in the in tubers of transgenic Plant #1 was quantified using both chemiluminescent $G_{M1}$-ELISA and chemiluminescent immunoblot assays as follows. Pentameric CTB fusion protein levels in transgenic potato plants and its affinity for $G_{M1}$-ganglioside were evaluated by quantitative chemiluminescent $G_{M1}$-ELISA assays. The microtiter plate was coated with 100 μl/well of monosialoganglioside $G_{M1}$ (3.0 μg/ml) (Sigma G-7641) in bicarbonate buffer, pH 9.6 (15 mM $Na_2CO_3$, 35 mM $NaHCO_3$) and incubated at 4° C. overnight. Wells were loaded with 100 μl/well of 10-fold serial dilutions of total soluble potato leaf or tuber protein in phosphate buffered saline (PBS) and incubated overnight at 4° C. The plate was washed three times in PBST (PBS containing 0.05% Tween-20). The wells were blocked by adding 300 μl/well of 1% bovine serum albumin (BSA) in PBS and incubated at 37° C. for 2 hours followed by washing three times with PBST. The wells were loaded with 100 μl/well of 1:5,000 dilution of rabbit anti-cholera toxin antibody (Sigma C-3062) and incubated for 2 hours at 37° C., followed by washing the wells three times with PBST. The plate was incubated with 100 μl/well of 1:50,000 dilution of alkaline phosphatase-conjugated anti-rabbit IgG (Sigma A-2556) for 2 hours at 37° C. and washed three times with PBST. The plate was finally incubated with 100 μl/well of Lumi-Phos® Plus (Lumigen, Inc. P-701) for 30 minutes at 37° C. and the enzyme-substrate reaction was measured in a Microlite™ ML3000 Microtiter® Plate Luminometer (Dynatech Laboratories).

In the chemiluminescent $G_{M1}$-ELISA method, the amount of plant CTB fusion protein was measured by comparison of chemiluminescent intensities from a known amount of bacterial CTB protein-antibody complex with that emitted from a known amount of transformed plant soluble protein. Two standard curves (1% and 0.1%) were generated based on the relative light units (RLU) measured for different amount of bacterial CTB. The RLU generated from serial dilutions of transgenic potato plant homogenates were plotted into the graph, and found to reside within the 0.1% and 0.01% curves, indicating that the fusion protein level in the transgenic potato tissue is slightly less than 0.1%.

In the chemiluminescent immunoblot method, luminescent intensities of bacterial and plant CTB protein bands blotted on Immun-Lite membranes after SDS-PAGE were measured by the Argus-100 low-light imager Data Analysis Program. The number of photons emitted from either bacterial CTB or plant CTB or plant CTB-NSP4 fusion protein bands were quantified, and their values compared to provide a semi-quantitative estimate of the amount of plant synthesized CTB fusion protein. Based on the amount of light emission detected from a known amount of bacterial CTB protein (100 ng), the amount of plant CTB fusion protein was calculated to be approximately 100 ng. The percent of chimeric protein in the plant was calculated based on the amount of soluble plant protein (100 μg) used in the assay. Based on this method, the percent of plant CTB protein was found to be approximately 0.1% of total soluble plant protein, a value in close agreement with measurements made by the chemiluminescent $G_{M1}$-ELISA method. Based on the results of the chemiluminescent ELISA and immunoblot assays, 1 g of callus tissues (fresh weight) obtained from auxin-induced potato leaves contained 10 μg of recombinant plant CTB-NSP4 fusion protein.

Pentamerization of CTB subunits is essential for its affinity for the natural receptor. In $G_{M1}$-ELISA binding assays, plant-produced chimeric protein and bacterial CTB demonstrated a strong affinity for $G_{M1}$-ganglioside but not for BSA, which was the bases of protein production level measurement. The ability of plant-derived CTB to bind $G_{M1}$-ganglioside indicates that the specific protein-ganglioside binding interactions between amino acid residues forming the $G_{M1}$ binding sites and the oligosaccharide moiety of $G_{M1}$-ganglioside are conserved. The strong binding efficiency of plant CTB conjugate for $G_{M1}$ indicate that molecular configurations of CTB moiety is well conserved. In addition, the absence of a monomeric form of chimera by immunoblot analysis indicates that predominant molecular species of chimeric protein is in the pentameric form, because monomeric CTB is unable to bind to $G_{M1}$-ganglioside. Therefore, the monomeric B subunit fusion polypeptide accumulated within the lumen of the ER of plant cells and self-assembly into pentameric $G_{M1}$ binding forms took place.

2) Method of Construction of a Transgenic Plant Producing a Fusion Protein Comprising the Immunodominant Epitope of the Murine Rotavirus Enterotoxin NSP4 Fused to the Cholera Toxin B Subunit and the ETEC Fimbrial Antigen CFA/I Fused to the Cholera Toxin A2 Subunit and Confirmation of Transformation.

According to another embodiment of the present invention, there is provided a transgenic plant producing a fusion protein comprising the twenty-two amino acid immunodominant epitope of the murine rotavirus enterotoxin NSP4 fused to the cholera toxin B subunit and the ETEC fimbrial antigen CFA/I fused to the cholera toxin A2 subunit. The immunodominant epitope of the murine rotavirus enterotoxin NSP4, the cholera toxin B subunit and the ETEC fimbrial antigen CFA/I function as antigens. The cholera toxin B subunit functions as an antigen and as an adjuvant. The cholera toxin A2 subunit functions as an adjuvant. The transgenic plant can be administered to a mammal to immunize the mammal against cholera, rotavirus and enterotoxigenic *E. coli* infection simultaneously.

As disclosed in greater detail below, the cholera toxin fusion proteins expressed in transformed potato tuber tissues assembled into a cholera holo-toxin-like oligomeric structure, which retained enterocyte membrane receptor $G_{M1}$-ganglioside binding affinity. Both serum and intestinal antibodies against NSP4, CFA/I and CTB were induced in orally immunized mice. Analysis of IL-2, IL-4 and INFg cytokine levels in spleen cells isolated from immunized mice indicated the presence of a strong Th1 immune response to the plant synthesized antigens. Fluorescent antibody based cell sorting (FACS) analysis of immunized mouse spleen cells showed an increase in $CD4^+$ but not $CD8^+$ memory cell populations. Following rotavirus challenge, passively immunized mouse pups showed a 50% reduction of diarrhea symptoms.

Figure 2:
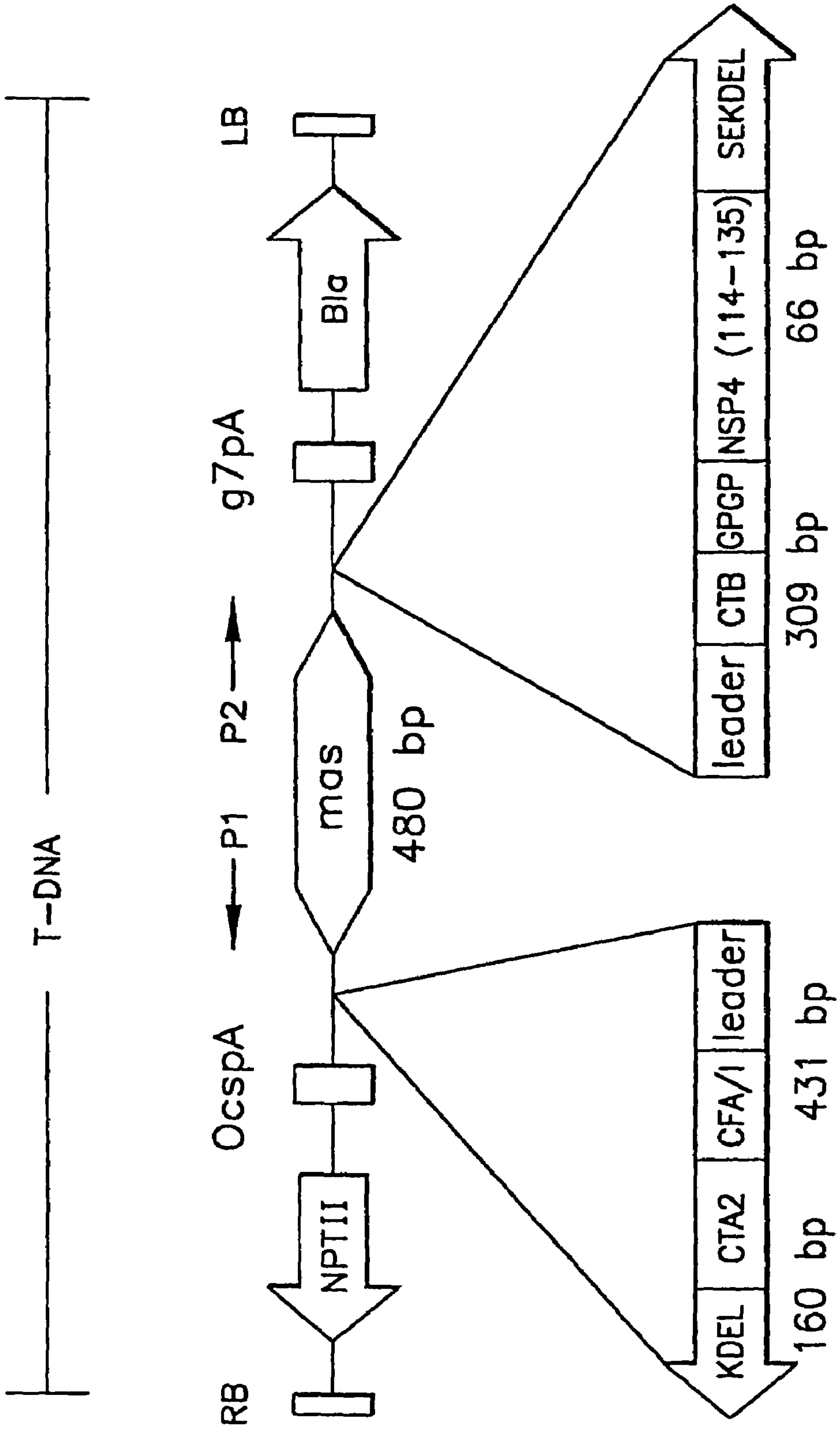
FIG. 2 is a diagram of the vector pPCV701CFA/I-CTB-NSP4.

Referring now to FIG. 2, there is shown a diagram of the vector used to prepare the transgenic plant. As can be seen, the vector pPCV701CFA/I-CTB-NSP4 contained four genes located within the transferred DNA (T-DNA) sequence flanked by the right and left border (RB and LB), and 25 bp direct repeats required for integration of the T-DNA into plant genomic DNA. The four genes were the CTBH:NSP4(114-135):SEKDEL coding sequence, SEQ ID NO:11, under control of the mas P2 promoter; the CFA/I:CTA2 (SEQ ID NO:12 and SEQ ID NO:13) coding sequence under control of the mas P1 promoter; an NPT II expression cassette in the T-DNA to provide resistance to kanamycin in plants for selection of transformed plants; and a β-lactamase cassette for resistance to ampicillin in *E. coli* and carbenicillin in *A. tumefaciens*. The g7pA polyadenylation signal was from the *A. tumefaciens* $T_L$-DNA gene 7. The OcspA polyadenylation signal is from the octopine synthase gene. Each cholera toxin fusion gene contains its own leader sequence and an ER retention signal. To increase the flexibility of the fusion protein, a four amino acid glycine-proline (GPGP) hinge region was inserted between the CTB and NSP4 peptides.

The expression vector pPCV701CFA/I-CTB-NSP4 was assembled from the parental plasmid pPCV701 in the following manner. A nucleotide sequence encoding the endoplasmic reticulum (ER) retention signal, SEKDEL, was first cloned into the plant expression vector pPCV701on the P2 site of the mannopine synthase (mas) dual P1, P2 promoter. The CTB gene, SEQ ID NO:1, were amplified by polymerase chain reaction (PCR) from the cholera toxin (ctxAB) operon in plasmid pPT42. The CTB 3' primer, SEQ ID NO:3, was designed to contain an oligonucleotide encoding the tetrapeptide hinge (Gly-Pro-Gly-Pro) to incorporate a degree of flexibility between the CTB and NSP4 peptides. A synthesized DNA fragment, SEQ ID NO:8, encoding the rotavirus enterotoxin NSP4 (114-135), epitope was inserted in frame between the CTB-hinge and the SEKDEL sequences. The CTA leader sequence, SEQ ID NO:14, and the CTA2 gene were amplified by PCR from the ctxAB operon and cloned into pPCv701 downstream of the mas P1 promoter region. A DNA fragment, (431 bp), SEQ ID NO:12, encoding the enterotoxigenic *E. coli* colonization factor CFA/I, was amplified from plasmid pIGx15A, and was inserted in frame between the CTA leader sequence, SEQ ID NO:14, and the CTA2 gene, SEQ ID NO:13. The whole CTA leader-CFA/I-CTA2 fusion gene is given as SEQ ID NO:15.

The resultant plant expression vector pPCV701CFA/I-CTB-NSP4, was introduced into *Agrobacterium tumefaciens* strain GV3101 pMP90RK. From sterile plants grown in culture medium in a light room, potato (*Solanum tuberosum* cv. Bintje) leaf tissue explants were transformed with *A. tumefaciens* harboring the plant expression vector pPCV701 CFA/I-CTB-NSP4. Transformed plants were regenerated from the explants on selection medium containing kanamycin. Prior to analysis of antigen gene expression, transgenic tubers were stimulated to produce high levels of the antigen proteins by incubation of tuber slices on growth medium containing auxin 2,4-D (2,4 dichlorophenoxy acetic acid) for 4 days at room temperature.

The presence of the CFA/I and CTB-NSP4 fusion proteins in the transformed plants were detected by immunoblot techniques as follows. Protein extracts from auxin stimulated transformed potato tubers containing 100 mg of total soluble protein (TSP) were loaded on a 10-15% SDS-PAGE gel with or without 5 minutes boiling prior to electrophoresis. The separated protein bands were transferred to nitrocellulose membrane by electroblotting on a semi-dry blotter (Sigma) at 30V, 60 mA for one and a half hours. The location of CTB, NSP4 and CFA/I proteins were identified by incubation of the blot in rabbit anti-CTB antiserum (Sigma 1:5000 dilution) overnight at room temperature followed by incubation in alkaline phosphatase-conjugated mouse anti-rabbit IgG (Sigma, at 1:10,000 dilution) for 2 hours at room temperature. Finally the membrane was incubated in the substrate BCIP/NPT (Sigma) for 10 min. The color reaction was stopped by washing the membrane several times in distilled water.

The bacterial CTB assembled into an oligomeric structure with a molecular weight of 45 kD, characteristic of the CTB pentamer. The transgenic plant produced CTB-NSP4 fusion peptide formed a 50 kDa oligomeric structure. The 5 kDa increase in molecular mass is consistent with the presence of the additional NSP4 peptide and the 6 amino acid SEKDEL signal. The plant sample containing both CFA/I-CTA2 and CTB-NSP4 fusion proteins showed the presence of a 70 kDa protein band, indicative of the insertion of CFA/I-CTA2 peptide into the CTB-NSP4 pentamer. The untransformed plant showed no cross reaction with the cholera toxin antibody. Immersion of the samples in boiling water for 5 minutes resulted in dissociation of the multimeric structures into monomers. The bacterial CTB monomer has a molecular mass of 11 kDa. The plant derived CTB-NSP4 multimer dissociated into an 18 kDa monomer which is consistent with the molecular mass of CTB plus NSP4.

3) Method of Immunizing a Mammal Against Infectious Diseases and Analysis of the Results.

A group of 10 CD-1 female mice each were fed 3 g transgenic potato tuber tissues containing a total of 7 mg of the recombinant fusion proteins previously determined by chemiluminescent ELISA on day 0, 5, 15, 23 and 56. Using the same feeding schedule, a group of 5 CD-1 mice each were fed 3 g of untransformed potato tuber tissues as a negative control. To evaluate the adjuvant effect of the CTB protein in the CTB-NSP4 fusion, CD1 mice (5 per group) were gavaged with pure NSP4 peptide with or without pure bacterial CTB (adjuvant) according to the same oral inoculation schedule. On day 13 after the final immunization, blood was taken from each mouse for serum antibody titer determination. Three mice per group were euthanized at three different time points: 13, 34 and 68 days after the fifth immunization. Intestinal washings were collected for mucosal antibody detection. Spleen cells from both immunized and negative control mice ($3\times10^6$ cells/well) were suspended in RPMI 1640 medium containing 10% fetal calf serum in duplicate samples, in 24 well tissue culture plates. After incubation for 72 hours at 37° C. in a humidified, 5% $CO_2$ incubator, supernatants from the spleen cell cultures were collected for assessment of IL-2, IL-4 and INFg secretion.

Following the five oral inoculations with transgenic potato tuber tissues, blood samples were collected and the serum anti CTB, NSP4 and CFA/I IgG titers were measured by ELISA methods used in our laboratory. Out of 10 mice, 8 generated serum IgG against CTB with a mean titer of 312.5±81.3. Of the 10 immunized mice, 8 developed serum IgG against NSP4 with a mean titer of 125±61.23. Out of the 10 immunized mice, 10 developed serum IgG against CFA/I with a mean titer of 84±44.2.

Intestinal IgG and IgA antibody titers against the three antigens were analyzed by chemiluminescent ELISA method used in our laboratory. Out of 10 immunized mice, 5 generated measurable intestinal anti-CTB antibody titers; 5 were found to have measurable intestinal anti-NSP4 antibody titers and 6 were found to have significant intestinal anti-CFA/I antibody titers. Negative control mice fed untransformed potato tuber tissues did not develop detectable specific serum or mucosal antibodies. Since the CTB pentamer can bind to $G_{M1}$ ganglioside located on the mucosal epithelial cell surface, induction of both systemic and mucosal antibodies in the immunized mice indicated the successful delivery of the cholera toxin fusion proteins to the GALT.

Adjuvant and carrier functions of CTB in the CTB-NSP4 fusion protein were determined by measuring serum anti-NSP4 antibody titers in mice from different vaccination groups. Mice fed the NSP4 peptide alone generated the lowest anti-NSP4 titer. Immunization with 7 mg of bacterial CTB (the same amount detected in the plant derived CTB-NSP4 fusion protein) increased the serum anti-NSP4 IgG titer approximately two fold. Mice fed 3 g transformed potato tuber tissues containing the CTB-NSP4 fusion protein developed the highest anti-NSP4 titer.

Small soluble proteins like the NSP4 22 amino acid epitope that are highly imunogenic by parenteral routes are frequently ineffective when administered orally unless a large dose of the protein is used. This result can be attributed to intestinal digestion and lack of tropism of the peptide for the gut associated lymphoid tissues. Either cholera holotoxin or the CTB subunit, which function as mucosal adjuvants can stimulate an immune response against co-administered protein antigens. Directly linking small antigens with CTB subunit not only results in specific targeting of the antigens to the mucosal immune system via specific enterocyte attachment but also increases the local antigen concentration at the mucosal surface, which may explain our detection of the strongest immune response directed against the CTB-NSP4 fusion protein.

The T lymphocyte populations in immunized mice were analyzed in immunized mice as follows. IL-2, IL-4 and INFg produced in the spleen cell culture supernatants were assayed by ELISA. Spleen lymphocytes were stained with fluorochrome-labeled monoclonal antibodies (mAb) for immunophenotyping. Two monoclonal antibody panels were constructed for three color analysis (fluoresceinisothiocanate (FITC), phycoerythrin (PE), and Cy-Chrome).

The first combination used, CD62L*FITC/CD4*PE/CD44*Cy-Chrome designates naïve and memory T helper cells. The second combination, CD62L*FITC/CD8b.2*PE/CD44*Cy-Chrome designates naïve and memory cytotoxic T cells. The spleen cells were resuspended at $10^6$ cells/ml in PBS and stained with fluorochrome-labeled mAbs. The labeled cells were analyzed by fluorescene activated cell sorting (FACS) to determine the T lymphocyte memory cell subpopulations.

Following multiple oral immunizations, the Il-2 and the INFg expression levels in spleen cells dramatically increased, reaching the highest level 34 days after the fifth immunization and decreasing to basal levels by 68 days after vaccination. Throughout this time period IL-4 levels remained low equivalent to that found in unimmunized mice. Thus, a cytokine expression pattern clearly indicated a Th1 lymphocyte mediated immune response generated by feeding mice the plant derived cholera toxin fusion antigens. Therefore, the overall cytokine secretion pattern of this multicomponent plant vaccine indicates a strong Th1 response. FACS analysis of spleen cells collected on day 13, 34 and 68 after the last immunization showed an elevated population of $CD4^+$ memory cells in comparison with the unimmunized mice through the two months after immunization. The $CD4^+$ memory cell subpopulation ($CD62^-$ $CD44^+$, gate R4) detected in the immunized mice was observed to be significantly higher than the $CD4^+$ memory cell subset in unimmunized mice. Thus, the generation of a significantly increased T helper memory cell population in the immunized mice indicated successful protective immunization mediated by the plant delivered antigens. The existence of increased numbers of memory cells provided the ability to mount a strong immune response following a second encounter with the same pathogen. The $CD8^+$ memory cell population detected in immunized mice did not show any significant increase over the unimmunized mouse negative control group.

Protection against rotavirus was evaluated as follows. Adult female CD-1 mice (five per group) were fed 3 g of untransformed or transgenic potato tuber slices once a week for four weeks. Immediately following the fourth immunization at maximum anti-NSP4 antibody titer, the mice were mated with uninfected males. After a 19-20 day gestation period, mouse pups were born to the immunized dams. On day 6 post parturition, each pup received one oral dose of simian rotavirus SA-11 in 50 ul PBS that contained 15 $DD_{50}$ (the virus dose determined empirically to cause diarrhea in 50% of the mouse pups). The mice were examined for the presence of diarrhea daily for 5 days following inoculation by gentle palpation of their abdomen to produce fecal pellets. The diarrhea score and the proportion of mice showing diarrhea symptoms in each study group were recorded.

The number of pups which developed diarrhea symptoms and the duration of the diarrhea was significantly reduced in the pups passively immunized with CTB-NSP4 fusion protein in comparison with pups born to unimmunized dams. On day 3 after rotavirus challenge, a 50% reduction of diarrhea symptoms was detected in the immunized pups. Complete resolution of diarrhea symptoms occurred 4 days after virus challenge in pups from immunized dams. To exclude the possibility of diarrhea reduction due to the presence of anti-CTB antibodies, pups born to dams immunized with plant derived CTB only were also challenged with an identical dose of rotavirus SA11. No reduction of diarrhea symptoms was detected in mice immunized with plant derived CTB alone. This experiment demonstrated that anti-NSP4 antibodies generated in orally immunized mice were passed on to the pups and protected them from the onset of rotavirus infection as well as significantly reducing the duration of the virus infection.

Therefore, according to one embodiment of the present invention, there is provided a method of inducing partial or complete immunity to an infectious disease in a mammal. The method comprises providing to the mammal for oral consumption an effective amount of a fusion protein according to the present invention. Preferably, the fusion protein is made in a transgenic plant. Further preferably, the fusion protein comprises a multimeric a cholera toxin B subunit and a first immunogenic antigen from a causal factor of the disease. In a preferred embodiment, the fusion protein additionally comprises a second immunogenic antigen from a causal factor of a mammalian disease fused to a cholera toxin subunit, such as cholera toxin subunit A2. The cholera toxin subunits act as adjuvants for the immunogenic antigens and, in the case of cholera toxin B subunit, also act as an immunogenic antigen against cholera infection.

The fusion protein can be provided to the mammal in a dose and frequency sufficient to render the mammal partially or completely immune from the first infectious disease, the second infection disease, cholera or a combination of the preceding. The specific dose and frequency are determined by well-known techniques as will be understood by those with skill in the art with reference to this disclosure.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method of inducing partial or complete immunity to gastroenteritis in a mammal comprising providing to the mammal for oral consumption an effective amount of a protein complex comprising five monomeric fusion proteins;

where each fusion protein comprises a cholera toxin B subunit linked to NSP4 antigen from rotavirus; and where the protein complex further comprises ETEC fimbrial antigen CFA/1 from enterotoxigenic *E. coli*.

2. A method for the prevention of multiple types of acute gastroenteritis simultaneously in a mammal comprising providing to the mammal for oral consumption an effective amount of a protein complex encoded by a DNA construct that encodes a protein complex comprising five monomeric fusion proteins when expressed in a plant cell;

where each fusion protein comprises a cholera toxin B subunit linked to NSP4 antigen from rotavirus; and where the protein complex further comprises ETEC fimbrial antigen CFA/1 from enterotoxigenic *E. coli*.

3. The method of claim 2, where the DNA construct comprises a bidirectional promoter controlling transcription of the DNA construct.

* * * * *

SEQUENCE LISTING

```
<160> NUMBER OF SEQ ID NOS: 15

<210> SEQ ID NO 1
<211> LENGTH: 376
<212> TYPE: DNA
<213> ORGANISM: Vibrio cholerae

<400> SEQUENCE: 1

atgattaaat taaaatttgg tgttttttt acagttttac tatcttcagc atatgcacat     60

ggaacacctc aaaatattac tgatttgtgt gcagaatacc acaacacaca aatacatacg    120

ctaaatgata agatattgtc gtatacagaa tctctagctg gaaacagaga gatggctatc    180
```

-continued

```
attactttta agaatggtgc aacttttcaa gtagaagtac caggtagtca acatatagat    240

tcacaaaaaa aagcgattga aaggatgaag gataccctga ggattgcata tcttactgaa    300

gctaaagtcg aaaagttatg tgtatggaat aataaaacgc ctcatgcgat tgccgcaatt    360

agtatggcaa attggc                                                    376


<210> SEQ ID NO 2
<211> LENGTH: 36
<212> TYPE: DNA
<213> ORGANISM: artificial sequence
<220> FEATURE:
<223> OTHER INFORMATION: completely synthesized

<400> SEQUENCE: 2

gctctagagc caccatgatt aaattaaaat ttggtg                               36


<210> SEQ ID NO 3
<211> LENGTH: 41
<212> TYPE: DNA
<213> ORGANISM: artificial sequence
<220> FEATURE:
<223> OTHER INFORMATION: completely synthesized

<400> SEQUENCE: 3

ctggagctcg ggccccggcc catttgccat actaattgcg g                          41


<210> SEQ ID NO 4
<211> LENGTH: 391
<212> TYPE: DNA
<213> ORGANISM: artificial sequence
<220> FEATURE:
<223> OTHER INFORMATION: completely synthesized hinge coding region and
      Vibrio cholerae

<400> SEQUENCE: 4

atgattaaat taaaatttgg tgtttttttt acagttttac tatcttcagc atatgcacat     60

ggaacacctc aaaatattac tgatttgtgt gcagaatacc acaacacaca aatacatacg    120

ctaaatgata agatattgtc gtatacagaa tctctagctg gaaacagaga gatggctatc    180

attactttta agaatggtgc aacttttcaa gtagaagtac caggtagtca acatatagat    240

tcacaaaaaa aagcgattga aaggatgaag gataccctga ggattgcata tcttactgaa    300

gctaaagtcg aaaagttatg tgtatggaat aataaaacgc ctcatgcgat tgccgcaatt    360

agtatggcaa attggcccag gcccgggata a                                   391


<210> SEQ ID NO 5
<211> LENGTH: 54
<212> TYPE: DNA
<213> ORGANISM: Vibrio cholerae

<400> SEQUENCE: 5

atggtaaaga taatatttgt gtttttttatt ttcttatcat cattttcata tgca          54


<210> SEQ ID NO 6
<211> LENGTH: 24
<212> TYPE: DNA
<213> ORGANISM: artificial sequence
<220> FEATURE:
<223> OTHER INFORMATION: completely synthesized

<400> SEQUENCE: 6

accaatacat tacactagca tctg                                            24
```

-continued

<210> SEQ ID NO 7
<211> LENGTH: 27
<212> TYPE: DNA
<213> ORGANISM: artificial sequence
<220> FEATURE:
<223> OTHER INFORMATION: completely synthesized

<400> SEQUENCE: 7
gactgagtgc gatattatgt gtaatac 27

<210> SEQ ID NO 8
<211> LENGTH: 66
<212> TYPE: DNA
<213> ORGANISM: Rotavirus sp.

<400> SEQUENCE: 8
gataggttga ctactagaga aattgaacaa gttgaattgt tgaagagaat ttacgataag 60
ttgact 66

<210> SEQ ID NO 9
<211> LENGTH: 60
<212> TYPE: DNA
<213> ORGANISM: artificial sequence
<220> FEATURE:
<223> OTHER INFORMATION: completely synthesized

<400> SEQUENCE: 9
gccgagctcg ataagttgac tactagggag attgagcaag ttgagttgtt gaagaggatt 60

<210> SEQ ID NO 10
<211> LENGTH: 60
<212> TYPE: DNA
<213> ORGANISM: artificial sequence
<220> FEATURE:
<223> OTHER INFORMATION: completely synthesized

<400> SEQUENCE: 10
gccgagctca caactcatcc ttctcagaag tcaacttatc gtaaatcctc ttcaacaact 60

<210> SEQ ID NO 11
<211> LENGTH: 488
<212> TYPE: DNA
<213> ORGANISM: artificial sequence
<220> FEATURE:
<223> OTHER INFORMATION: Vibrio cholerae and Rotavirus sp.

<400> SEQUENCE: 11
atgattaaat taaaatttgg tgtttttttt acagttttac tatcttcagc atatgcacat 60
ggaacacctc aaaatattac tgatttgtgt gcagaatacc acaacacaca aatacatacg 120
ctaaatgata agatattgtc gtatacagaa tctctagctg gaaacagaga gatggctatc 180
attactttta agaatggtgc aacttttcaa gtagaagtac caggtagtca acatatagat 240
tcacaaaaaa aagcgattga aaggatgaag gataccctga ggattgcata tcttactgaa 300
gctaaagtcg aaaagttatg tgtatggaat aataaaacgc ctcatgcgat tgccgcaatt 360
agtatggcaa attggcccag gcccgggaga gctcgataag ttgactacta gggagattga 420
gcaagttgag ttgttgaaga ggatttacga taagttgact tctgagaagg atgagttgtg 480
agctctaa 488

-continued

```
<210> SEQ ID NO 12
<211> LENGTH: 444
<212> TYPE: DNA
<213> ORGANISM: Escherichia coli

<400> SEQUENCE: 12

gtagagaaaa atattactgt aacagctagt gttgatcctg taattgatct tttgcaagct     60

gatggcaatg ctctgccatc agctgtaaag ttagcttatt ctcccgcatc aaaaactttt    120

gaaagttaca gagtaatgac tcaagttcat acaaacgatg caactaaaaa agtaattgtt    180

aaacttgctg atacaccaca gcttacagat gttctgaatt caactgttca aatgcctatc    240

agtgtgtcat ggggaggaca agtattatct tctacaacag ccaaagaatt tgaagctgct    300

gctttgggat attctgcatc cggtgtaaat ggcgtatcat cttctcaaga gttagtaatt    360

agcgctgcac ctaaaactgc cggtaccgcc ccaactgcag gaaactattc aggagtagta    420

tctcttgtaa tgactttggg atcc                                           444


<210> SEQ ID NO 13
<211> LENGTH: 141
<212> TYPE: DNA
<213> ORGANISM: Vibrio cholerae

<400> SEQUENCE: 13

atcagtaata cttgcgatga aaaaacccaa agtctaggtg taaaattcct tgacgaatac     60

caatctaaag ttaaaagaca aatattttca ggctatcaat ctgatattga tacacataat    120

agaattaaag atgagttgtg a                                              141


<210> SEQ ID NO 14
<211> LENGTH: 54
<212> TYPE: DNA
<213> ORGANISM: Vibrio cholerae

<400> SEQUENCE: 14

atggtaaaga taatatttgt gttttttatt ttcttatcat cattttcata tgca           54


<210> SEQ ID NO 15
<211> LENGTH: 651
<212> TYPE: DNA
<213> ORGANISM: artificial sequence
<220> FEATURE:
<223> OTHER INFORMATION: Vibrio cholerai and Escherichia coli

<400> SEQUENCE: 15

atggtaaaga taatatttgt gttttttatt ttcttatcat cattttcata tgcagtcgac     60

gtagagaaaa atattactgt aacagctagt gttgatcctg taattgatct tttgcaagct    120

gatggcaatg ctctgccatc agctgtaaag ttagcttatt ctcccgcatc aaaaactttt    180

gaaagttaca gagtaatgac tcaagttcat acaaacgatg caactaaaaa agtaattgtt    240

aaacttgctg atacaccaca gcttacagat gttctgaatt caactgttca aatgcctatc    300

agtgtgtcat ggggaggaca agtattatct tctacaacag ccaaagaatt tgaagctgct    360

gctttgggat attctgcatc cggtgtaaat ggcgtatcat cttctcaaga gttagtaatt    420

agcgctgcac ctaaaactgc cggtaccgcc ccaactgcag gaaactattc aggagtagta    480

tctcttgtaa tgactttggg atccgtcgac atcagtaata cttgcgatga aaaaacccaa    540

agtctaggtg taaaattcct tgacgaatac caatctaaag ttaaaagaca aatattttca    600

ggctatcaat ctgatattga tacacataat agaattaaag atgagttgtg a             651
```